United States Patent
Greenberg et al.

(10) Patent No.: US 8,483,837 B2
(45) Date of Patent: Jul. 9, 2013

(54) SELECTABLE FILTERS FOR A VISUAL PROSTHESIS

(75) Inventors: Robert J. Greenberg, Los Angeles, CA (US); Kelly H. McClure, Simi Valley, CA (US); Sanjay R. Gaikwad, Valencia, CA (US)

(73) Assignee: Second Sight Medical Products, Inc., Sylmar, CA (US)

( * ) Notice: Subject to any disclaimer, the term of this patent is extended or adjusted under 35 U.S.C. 154(b) by 140 days.

(21) Appl. No.: 13/097,449

(22) Filed: Apr. 29, 2011

(65) Prior Publication Data

US 2011/0270353 A1 Nov. 3, 2011

Related U.S. Application Data

(60) Provisional application No. 61/330,098, filed on Apr. 30, 2010.

(51) Int. Cl.
*A61N 1/00* (2006.01)

(52) U.S. Cl.
USPC .......................................... 607/53

(58) Field of Classification Search
USPC .......................................... 607/53
See application file for complete search history.

(56) References Cited

U.S. PATENT DOCUMENTS

| 5,109,844 | A | 5/1992 | de Juan, Jr. et al. |
| 5,935,155 | A | 8/1999 | Humayun et al. |
| 6,400,989 | B1 | 6/2002 | Eckmiller |
| 6,458,157 | B1 | 10/2002 | Suaning |
| 2004/0088026 | A1 | 5/2004 | Chow et al. |
| 2007/0027503 | A1* | 2/2007 | Greenberg et al. ............ 607/54 |
| 2008/0086206 | A1* | 4/2008 | Nasiatka et al. ............. 623/6.14 |
| 2008/0183244 | A1 | 7/2008 | Greenberg et al. |

* cited by examiner

*Primary Examiner* — George Manuel
(74) *Attorney, Agent, or Firm* — Scott B. Dunbar

(57) ABSTRACT

The present invention is a visual prosthesis including a visor with an embedded camera and changeable optical filters to limit light entering the lens of the camera. This invention will allow use of custom filters to limit light intensity or certain light frequencies sent to the camera of the visual prosthesis in a variety of brightness conditions which will remove glare. It will allow modification of the color of the light sent to camera of the visual prosthesis to respond to different environments. Users may choose the best filter to suit their needs in real time.

20 Claims, 7 Drawing Sheets

SELECTABLE FILTERS FOR A VISUAL PROSTHESIS

CROSS REFERENCE TO RELATED APPLICATIONS

This application claims priority to U.S. Provisional Ser. No. 61/330,098 for "Selectable Filter for a Visual Prosthesis" filed on Apr. 30, 2010, and is related to U.S. patent application Ser. No. 11/893,260, filed Aug. 15, 2007 for "Visor for a Visual Prosthesis, published as 2008/0154336, both of which are incorporated herein by reference in their entirety.

GOVERNMENT RIGHTS NOTICE

This invention was made with government support under grant No. R24EY12893-01, awarded by the National Institutes of Health. The government has certain rights in the invention.

FIELD

The present disclosure is generally directed to neural stimulation and more specifically to a visual prosthetic apparatus for retinal stimulation.

BACKGROUND

As intraocular surgical techniques have advanced, it has become possible to apply stimulation on small groups and even on individual retinal cells to generate focused phosphenes through devices implanted within the eye itself. This has sparked renewed interest in developing methods and apparatuses to aid the visually impaired. Specifically, great effort has been expended in the area of intraocular retinal prosthesis devices in an effort to restore vision in cases where blindness is caused by photoreceptor degenerative retinal diseases such as retinitis pigmentosa and age related macular degeneration which affect millions of people worldwide.

Neural tissue can be artificially stimulated and activated by prosthetic devices that pass pulses of electrical current through electrodes on such a device. The passage of current causes changes in electrical potentials across visual neuronal membranes, which can initiate visual neuron action potentials, which are the means of information transfer in the nervous system.

Based on this mechanism, it is possible to input information into the nervous system by coding the information as a sequence of electrical pulses which are relayed to the nervous system via the prosthetic device. In this way, it is possible to provide artificial sensations including vision.

One typical application of neural tissue stimulation is in the rehabilitation of the blind. Some forms of blindness involve selective loss of the light sensitive transducers of the retina. Other retinal neurons remain viable, however, and may be activated in the manner described above by placement of a prosthetic electrode device on the inner (toward the vitreous) retinal surface (epiretinal). This placement must be mechanically stable, minimize the distance between the device electrodes and the visual neurons, and avoid undue compression of the visual neurons.

In 1986, Bullara (U.S. Pat. No. 4,573,481) patented an electrode assembly for surgical implantation on a nerve. The matrix was silicone with embedded iridium electrodes. The assembly fit around a nerve to stimulate it.

Dawson and Radtke stimulated cat's retina by direct electrical stimulation of the retinal ganglion cell layer. These experimenters placed nine and then fourteen electrodes upon the inner retinal layer (i.e., primarily the ganglion cell layer) of two cats. Their experiments suggested that electrical stimulation of the retina with 30 to 100 uA current resulted in visual cortical responses. These experiments were carried out with needle-shaped electrodes that penetrated the surface of the retina (see also U.S. Pat. No. 4,628,933 to Michelson).

The Michelson '933 apparatus includes an array of photosensitive devices on its surface that are connected to a plurality of electrodes positioned on the opposite surface of the device to stimulate the retina. These electrodes are disposed to form an array similar to a "bed of nails" having conductors which impinge directly on the retina to stimulate the retinal cells. U.S. Pat. No. 4,837,049 to Byers describes spike electrodes for neural stimulation. Each spike electrode pierces neural tissue for better electrical contact. U.S. Pat. No. 5,215,088 to Norman describes an array of spike electrodes for cortical stimulation. Each spike pierces cortical tissue for better electrical contact.

The art of implanting an intraocular prosthetic device to electrically stimulate the retina was advanced with the introduction of retinal tacks in retinal surgery. De Juan, et al. at Duke University Eye Center inserted retinal tacks into retinas in an effort to reattach retinas that had detached from the underlying choroid, which is the source of blood supply for the outer retina and thus the photoreceptors. See, e.g., de Juan, et al., 99 Am. J. Ophthalmol. 272 (1985). These retinal tacks have proved to be biocompatible and remain embedded in the retina, with the choroid/sclera, effectively pinning the retina against the choroid and the posterior aspects of the globe. Retinal tacks are one way to attach a retinal array to the retina. U.S. Pat. No. 5,109,844 to de Juan describes a flat electrode array placed against the retina for visual stimulation. U.S. Pat. No. 5,935,155 to Humayun describes a retinal prosthesis for use with the flat retinal array described in de Juan.

Off the shelf miniature cameras used in visual prostheses, or other common miniaturized cameras suitable for mounting in a pair of glasses, have difficulty responding to high intensity lighting conditions and different cameras can have different color responses, which is not ideal. Electronic compensation is not possible in some cases where the camera is saturated. Further electronic compensation requires processing time that can be better allocated to other visual prosthesis functions.

SUMMARY

The present invention is a visual prosthesis including a visor with an embedded camera and changeable optical filters to limit light entering the lens of the camera. This invention will allow use of custom filters to limit light intensity or certain light frequencies sent to the camera of the visual prosthesis in a variety of brightness conditions which will remove glare. It will allow modification of the color of the light sent to camera of the visual prosthesis to respond to different environments. Users may choose the best filter to suit their needs in real time.

DETAILED DESCRIPTION

Figure 1:
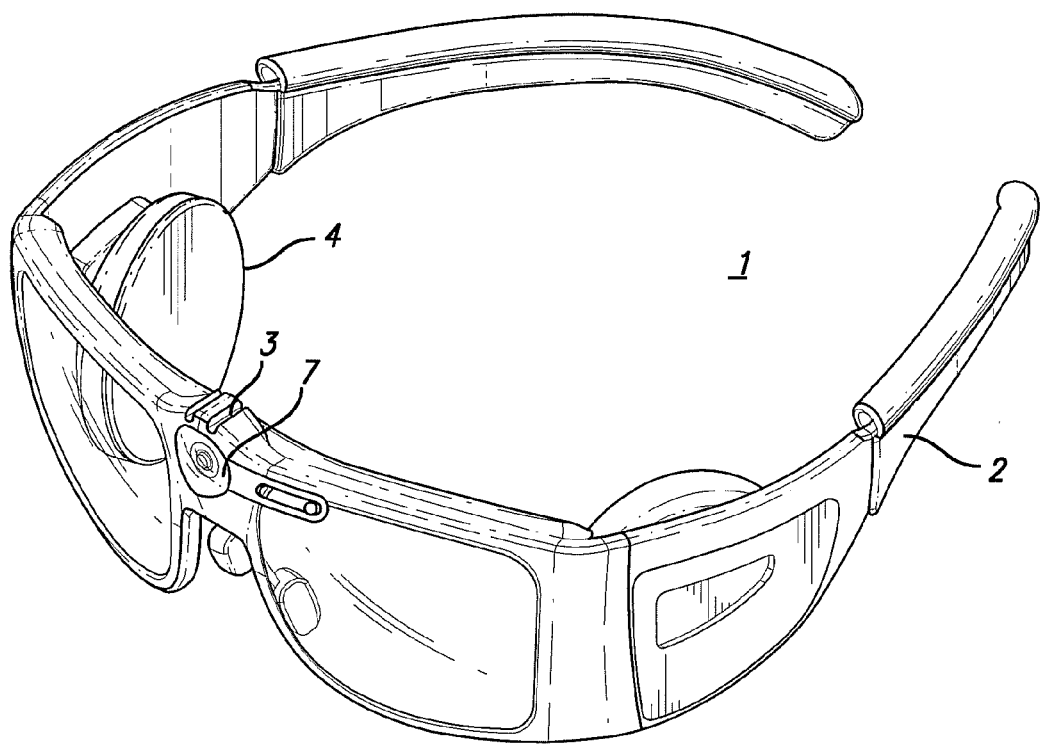
FIG. 1 is a schematic view of the visor of the preferred visual prosthesis.

The glasses or visor 1 may have a sliding lens cover 7 that can be placed in front of the camera 3 lens on the visor 1 as shown in FIG. 1. The camera may be mounted in the bridge of the glasses. The sliding lens cover 7 may be made of dark shade transparent material to limit the intensity of light falling on the camera 3 lens. Based on the ambient light conditions, the user can utilize this feature to limit bright light. The sliding cover 7 material may provide a choice of ND (Normal Density), Graded Neutral Density, normal density plus ultraviolet (ND+UV), Color filters, high contrast filters, or there filters as are commonly known for use for eye glasses. Desired available filters can be combined into a single lens cover and placed linearly side by side. Incorporating a longer sliding travel, each section of filter can come in front of the lens for desired effect.

Figure 2:
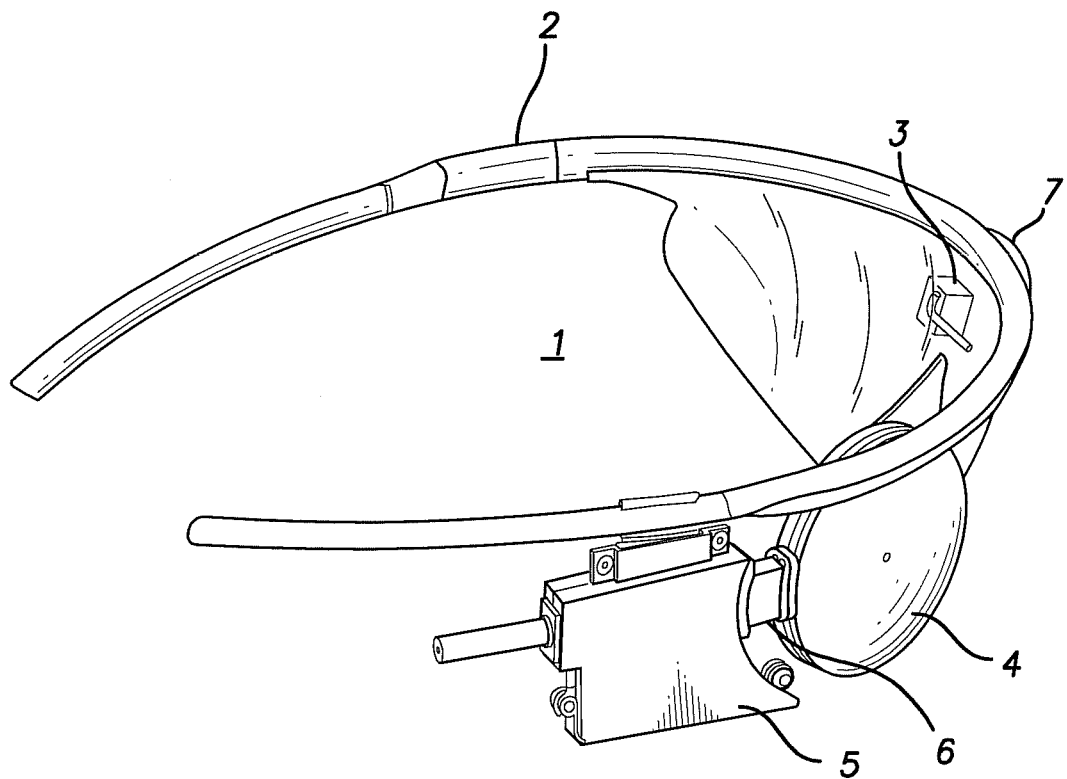
FIGS. 2 and 3 show perspective views of the preferred visor of a visual prosthetic apparatus.
Figure 3:
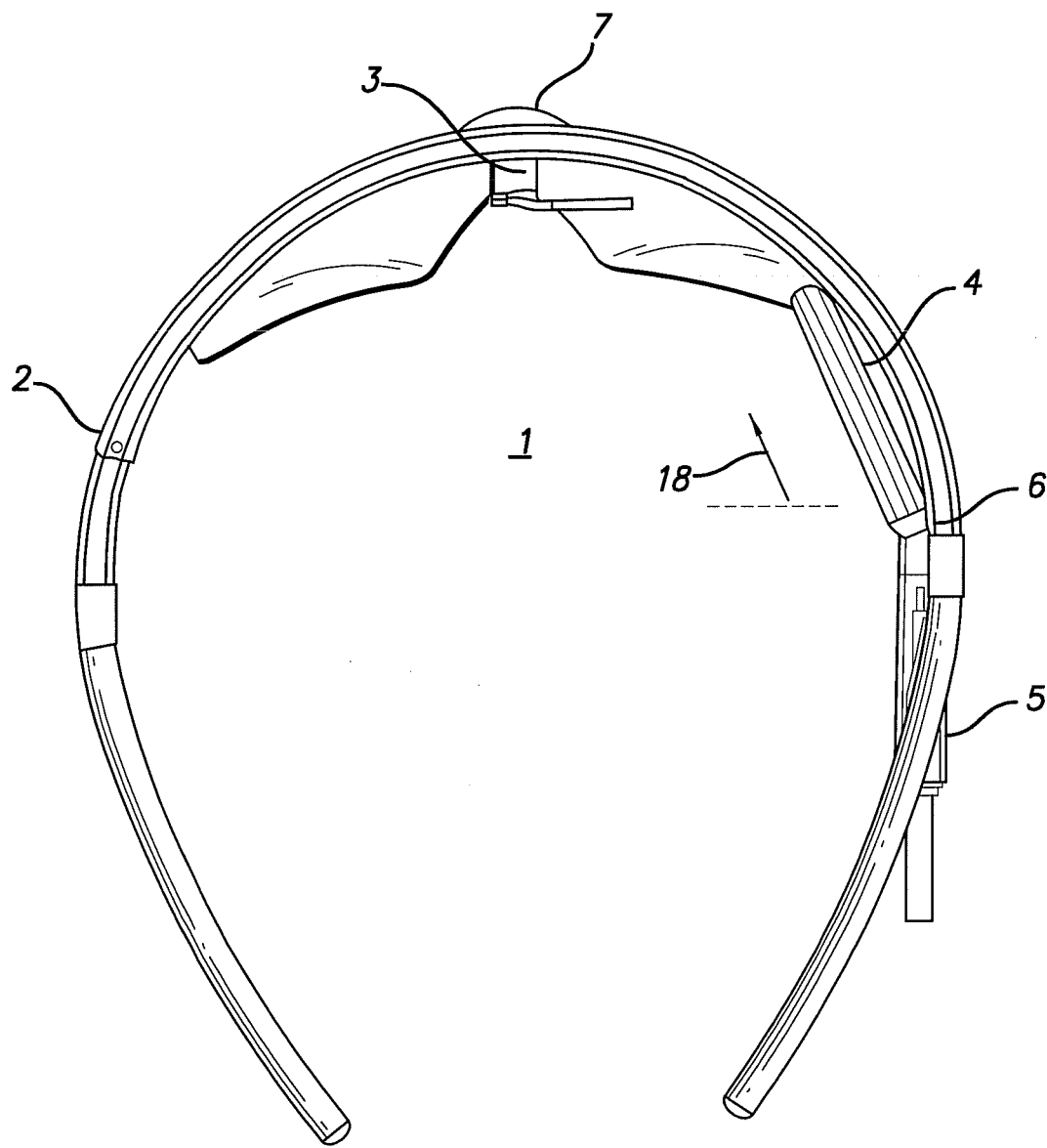

FIGS. 2 and 3 show two different perspective views of an external portion of a visual prosthetic apparatus according to the present disclosure. 'External' is here meant to indicate that the portion is external to the human body, and not implanted therein. The external portion includes the visor 1 and is adapted to be used in combination with an implantable portion 23, shown in FIGS. 6 and 7. Turning to FIGS. 2 and 3, the external portion 1 comprises a frame 2 holding a camera 3, an external coil arrangement 4 and a mounting system 5 for the external coil arrangement 4. The external coil arrangement 4 comprises external transmitting and receiving radio-frequency (RF) coils adapted to be used together and communicate with an internal RF coil (later shown in FIGS. 6 and 7). The mounting system 5 also encloses the RF circuitry for modulating, demodulating, transmitting, and receiving an RF signal. External coil arrangement 4 and mounting system 5 are connected by a flexible connector 6.

Figure 4:
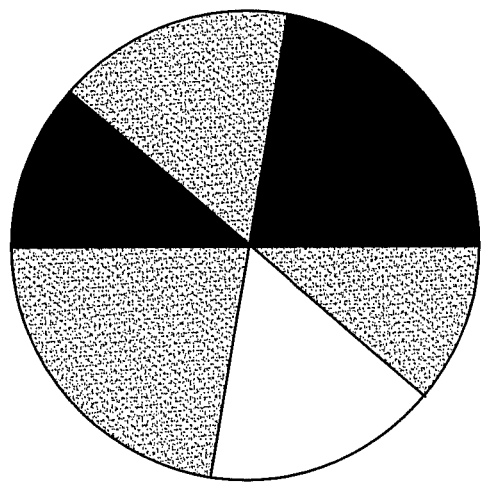
FIG. 4 is a shade wheel for an alternative embodiment.
Figure 5:
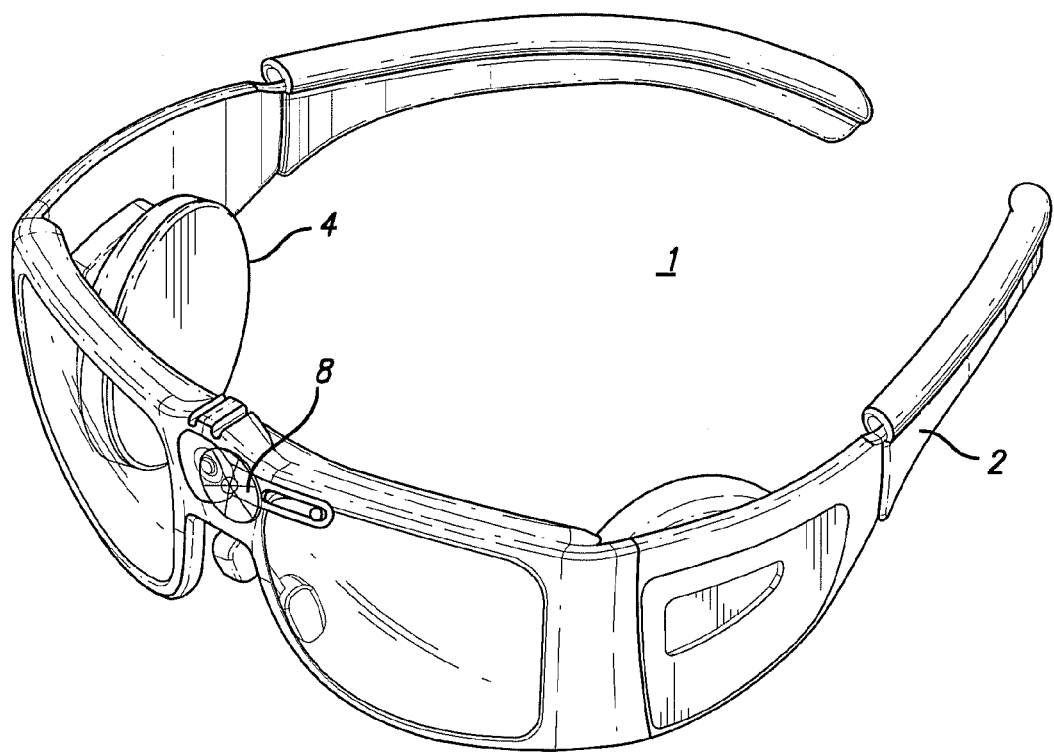
FIG. 5 is the alternative visor using a shade wheel.

Alternatively the filter lens cover can be hinged from the top of the frame and flipped down when needed (not shown). Alternatively the lens may be hinged to the side of the camera and flipped sideway when needed (also not shown). Referring to FIGS. 4 and 5, alternatively the filters can be arranged on a composite circular lens cover in pie chart segment as shown in FIG. 4. FIG. 5 shows the composite circular lens cover 8 in front of the camera 4 lens. The composite circular lens cover 8 is attached to a bearing at its center and mounted to glasses. The rotating circular lens cover 8 will allow the desired filter section to be placed in front of the camera 3 lens. Another Alternate embodiment is to integrate the actual lens cover mounted into the glasses frame so that it is not visible from the front. The integration can be applicable for both linear travel lens cover (FIG. 1) as well as rotating lens cover (FIG. 5).

Figure 6:
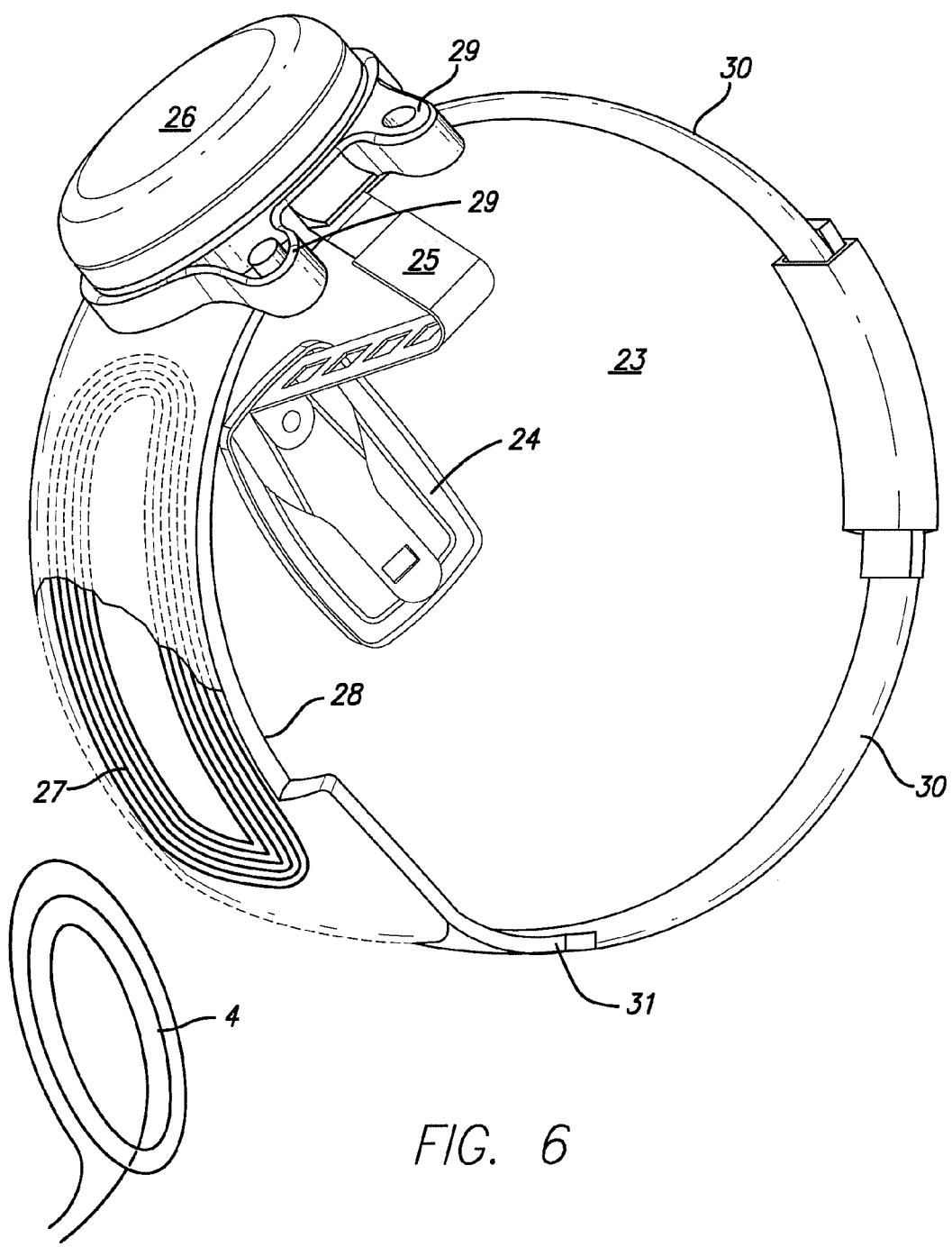
FIG. 6 shows a perspective view of the implantable portion of the visual prosthesis.

FIG. 6 shows a perspective view of an implantable portion 23 of a retinal prosthesis as disclosed. An electrode array 24 is mounted by a retinal tack or similar means to the epiretinal surface. The electrode array 24 is electrically coupled by a cable 25, which can pierce the sclera and be electrically coupled to an electronics package 26 external to the sclera. Electronic package 26 includes the RF receiver and electrode drivers.

The electronics package 26 can be electrically coupled to the secondary inductive coil 27. In one aspect, the secondary inductive coil 27 is made from wound wire. Alternatively, the secondary inductive coil may be made from a thin film polymer sandwich with wire traces deposited between layers of thin film polymer. The secondary coil receives power and data from the primary coil 4 which is external to the body. The electronics package 26 and secondary inductive coil 27 are held together by a molded body 28. The molded body 28 may also include suture tabs 29. The molded body narrows in a fan tail 31 to form a strap 30 which surrounds the sclera and holds the molded body 28, secondary inductive coil 27, and electronics package 26 in place. The molded body 28, suture tabs 29 and strap 30 are preferably an integrated unit made of silicone elastomer. Silicone elastomer can be formed in a pre-curved shape to match the curvature of a typical sclera. Furthermore, silicone remains flexible enough to accommodate implantation and to adapt to variations in the curvature of an individual sclera. In one aspect, the secondary inductive coil 27 and molded body 28 are oval shaped, and in this way, a strap 30 can better support the oval shaped coil.

The entire implantable portion 23 is attached to and supported by the sclera of a subject. The eye moves constantly. The eye moves to scan a scene and also has a jitter motion to prevent image stabilization. Even though such motion is useless in the blind, it often continues long after a person has lost their sight. By placing the device under the rectus muscles with the electronics package in an area of fatty tissue between the rectus muscles, eye motion does not cause any flexing which might fatigue, and eventually damage, the device.

Figure 7:
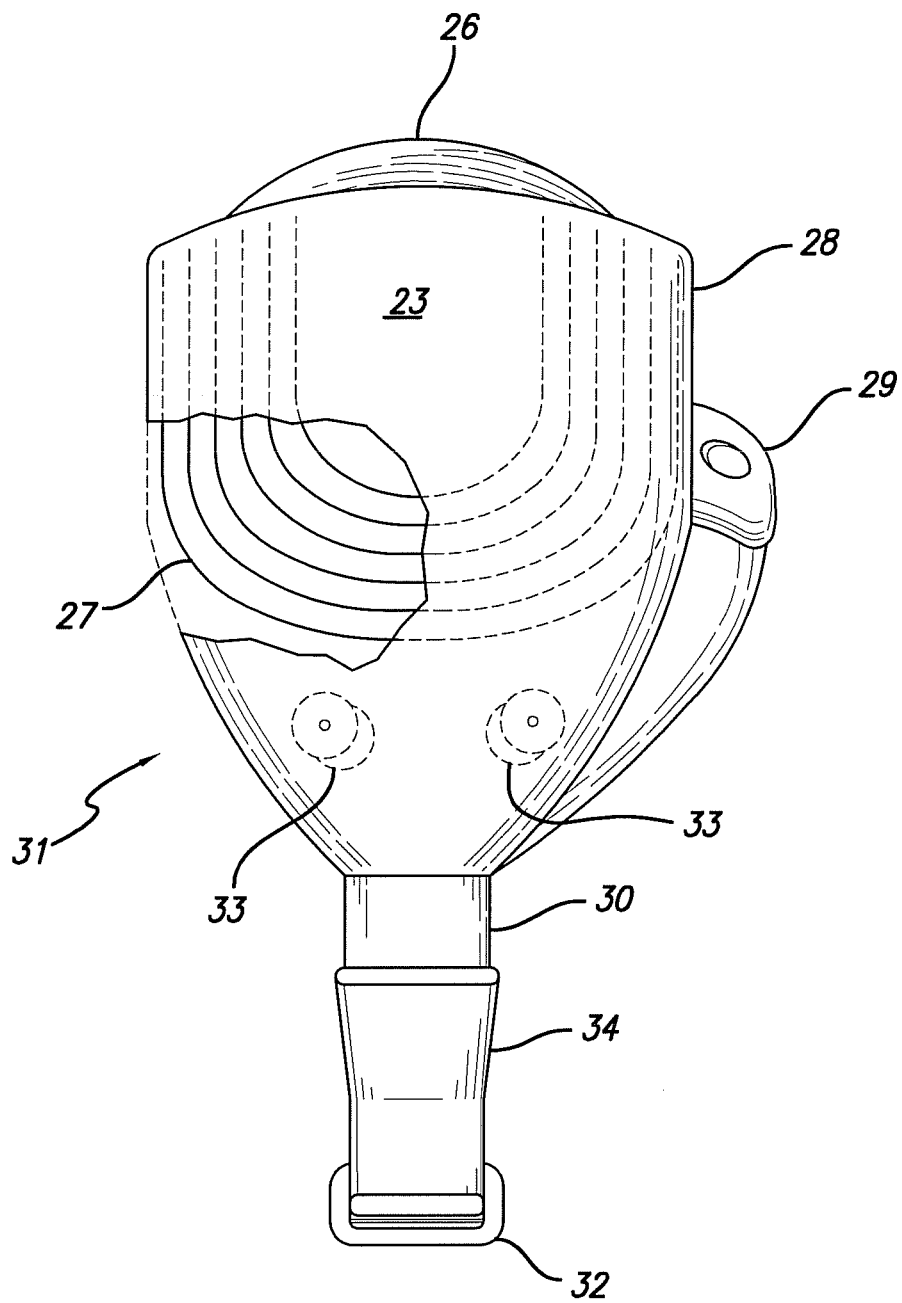
FIG. 7 is a side view of the implantable portion of the visual prosthesis.

FIG. 7 shows a side view of the implantable portion of the retinal prosthesis, in particular, emphasizing the fan tail 31. When the retinal prosthesis is implanted, the strap 30 has to be passed under the eye muscles to surround the sclera. The secondary inductive coil 27 and molded body 28 should also follow the strap under the lateral rectus muscle on the side of the sclera. The implantable portion 23 of the retinal prosthesis is very delicate. It is easy to tear the molded body 28 or break wires in the secondary inductive coil 27. In order to allow the molded body 28 to slide smoothly under the lateral rectus muscle, the molded body is shaped in the form of a fan tail 31 on the end opposite the electronics package 26. Element 32 shows a retention sleeve, while elements 33 and 34 show holes for surgical positioning and a ramp for surgical positioning, respectively.

In summary, a visual prosthetic apparatus is provided. The apparatus provides a means for adjusting the light received by the camera. While the invention has been described by means of specific embodiments and applications thereof, it is understood that numerous modifications and variations could be made thereto by those skilled in the art without departing from the spirit and scope of the invention. It is therefore to be understood that within the scope of the claims, the invention may be practiced otherwise than as specifically described herein.

What is claimed is:

1. A visual prosthetic apparatus comprising:
   an implantable portion and an external portion,
   wherein the implantable portion comprises an data receiver, and an array of electrodes,
   wherein the external portion comprises a frame, a camera having a lens mounted on the frame and a transmitter sending visual data to the implanted portion, and
   a movable lens cover, supported by the frame in front of the lens, to affect the light entering the lens of the camera.

2. The visual prosthetic apparatus according to claim 1, wherein the lens cover is movable in a linear direction.

3. The visual prosthetic apparatus according to claim 2, wherein the lens cover has multiple filters selectable by movement of the lens cover relative to the frame.

4. The visual prosthetic apparatus according to claim 1, wherein the lens cover is movable in a circular directions.

5. The visual prosthetic apparatus according to claim 4, wherein the lens cover has multiple filters selectable by movement of the lens cover relative to the frame.

6. The visual prosthetic apparatus according to claim 1, wherein the lens cover is attached to the frame by a hinge.

7. The visual prosthetic apparatus according to claim 1, wherein the lens cover includes a normal density filter.

8. The visual prosthetic apparatus according to claim 1, wherein the lens cover includes a Graded Neutral Density filter.

9. The visual prosthetic apparatus according to claim 1, wherein the lens cover includes an ultraviolet light filter.

10. The visual prosthetic apparatus according to claim 1, wherein the lens cover includes a color filter.

11. A visual prosthetic apparatus for retinal stimulation comprising:
   an implantable portion and an external portion,
   wherein the implantable portion comprises an RF receiver, an internal coil, and an array of electrodes,
   wherein the external portion comprises a frame, a camera having a lens mounted on the frame and an external coil mounted on the frame, and
   a movable lens cover, supported by the frame in front of the lens, to affect the light entering the lens of the camera.

12. The visual prosthetic apparatus according to claim 11, wherein the lens cover is movable in a linear direction.

13. The visual prosthetic apparatus according to claim 12, wherein the lens cover has multiple filters selectable by movement of the lens cover relative to the frame.

14. The visual prosthetic apparatus according to claim 11, wherein the lens cover is movable in a circular directions.

15. The visual prosthetic apparatus according to claim 14, wherein the lens cover has multiple filters selectable by movement of the lens cover relative to the frame.

16. The visual prosthetic apparatus according to claim 11, wherein the lens cover is attached to the frame by a hinge.

17. The visual prosthetic apparatus according to claim 11, wherein the lens cover includes a normal density filter.

18. The visual prosthetic apparatus according to claim 11, wherein the lens cover includes a Graded Neutral Density filter.

19. The visual prosthetic apparatus according to claim 11, wherein the lens cover includes an ultraviolet light filter.

20. The visual prosthetic apparatus according to claim 11, wherein the lens cover includes a color filter.

* * * * *